United States Patent
Kaushik et al.

(10) Patent No.: US 7,348,435 B2
(45) Date of Patent: Mar. 25, 2008

(54) PROCESS FOR PRODUCING CYANOPIPERIDINE

(75) Inventors: Vijay Kumar Kaushik, J.P. Nagar (IN); Nanhe Lal Chaurasia, J.P. Nagar (IN); Pradeep Kumar Verma, J.P. Nagar (IN); Ashutosh Agarwal, Ghaziabad (IN)

(73) Assignee: Jubilant Organosys Limited, Noida (IN)

( * ) Notice: Subject to any disclaimer, the term of this patent is extended or adjusted under 35 U.S.C. 154(b) by 229 days.

(21) Appl. No.: 11/195,728

(22) Filed: Aug. 3, 2005

(65) Prior Publication Data
US 2006/0084808 A1 Apr. 20, 2006

(30) Foreign Application Priority Data
Oct. 18, 2004 (IN) .................. 2035/DEL/2004

(51) Int. Cl.
*C07D 211/56* (2006.01)
(52) U.S. Cl. .................................................... 546/246
(58) Field of Classification Search ................ 546/215, 546/246, 286
See application file for complete search history.

(56) References Cited
OTHER PUBLICATIONS
Orjales et al., J. Med. Chem. Nov. 1, 2003, 46, 5512-5532.*
* cited by examiner

*Primary Examiner*—Bernard Dentz
*Assistant Examiner*—David E Gallis
(74) *Attorney, Agent, or Firm*—Oblon, Spivak, McClelland, Maier & Neustadt, P.C.

(57) ABSTRACT

The present invention relates to an improved and single step process for producing cyanopiperidine by dehydrating respective piperidine carboxamide employing a suitable dehydrating agent.

10 Claims, No Drawings

PROCESS FOR PRODUCING CYANOPIPERIDINE

FIELD OF THE INVENTION

The present invention relates to a process for producing cyanopiperidines. More specifically, but without restriction to the particular embodiments hereinafter described, the present invention relates to an improved single step process for producing cyanopiperidines by dehydrating the respective piperidine carboxamide employing a suitable dehydrating agent.

BACKGROUND OF THE INVENTION

Cyanopiperidines, especially 4-cyanopiperidine, are used as intermediates for the production of pharmacologically valuable substances like antidepressants, anti-inflammatory and immunomodulators. 4-Cyanopiperidine is also used as a starting material for the preparation of a large number of piperidine derivatives.

Several different conventional methods for producing cyanopiperidines are known.

U.S. Pat. No. 5,869,663 to Emonds-Alt et al., discloses a single step process for producing 4-cyanopiperidine from isonipecotamide (or piperidine-4-carboxamide) by dehydrating with phosphorous oxychloride, addition of concentrated mass to maintain pH—13, followed by multiple extractions with dichloromethane and ether. This process is laborious and is not commercially lucrative due to the involvement of multiple extractions with a mixture of low boiling solvents and generation of significant amounts of effluents. Moreover, the yield with above process is very low (approx. 25% w/w, 30% molar).

U.S. Pat. No. 4,284,636 to Carr et al., discloses the preparation of 4-cyanopiperidine by reacting piperidine-4-carboxamide with triflouroacetic anhydride and refluxing the reaction mass for 19 hours. Trifluoroacetic anhydride and trifluoroacetic acid are removed in vacuo and residual 4-cyano-1-fluoroacetyl piperidine is added to aqueous solution of potassium carbonate and methanol. Methanol is recovered and benzene is added to the concentrated reaction mass. Workup and distillation in vacuo gives the desired product 23%, w/w and 27% molar yield of 4-cyanopiperidine. The major drawbacks of this process are that it involves several steps, usage of hazardous chemicals, multiple solvents, generation of effluents and lower yields, thus, rendering the process industrially unattractive.

Therefore, there is a need to develop an improved process for producing cyanopiperidines, in particular 4-cyanopiperidine, which overcomes the disadvantages associated with the processes discussed above.

SUMMARY OF THE INVENTION

It is, therefore, an object of the present invention to improve upon the limitations of the processes described above. These and other objects are attained in accordance with the present invention wherein there is provided several embodiments of an improved and, optionally, single step process for producing cyanopiperidines by dehydrating piperidine carboxamides using the dehydrating agent thionyl chloride to produce cyanopiperidine with higher yields and selectivity. Thus, the present invention provides a process for producing a cyanopiperidine, comprising treating a piperidine carboxamide with thionyl chloride.

In one preferred embodiment, a reaction mass is produced from the reaction of the piperidine carboxamide with the thionyl chloride and the process further comprises neutralizing the reaction mass, extracting the neutralized reaction mass with an aromatic hydrocarbon solvent, distilling out the hydrocarbon solvent to produce a crude product and distilling the crude product under vacuum to obtain the cyanopiperidine.

In another preferred embodiment of the present invention, there is provided an improved process for producing 4-cyanopiperidine, wherein the process comprises treating piperidine-4-carboxamide with thionyl chloride, neutralizing the resultant reaction mass with caustic lye and extracting the desired product from the reaction mass using a suitable non-polar solvent.

In another preferred embodiment of the present invention, there is provided an improved and, optionally, single step process, wherein the process comprises dehydrating the piperidine-4-carboxamide by treating piperidine-4-carboxamide with thionyl chloride at a temperature of 10°-150° C., preferably 20°-100° C., to produce 4-cyanopiperidine, where the ratio of piperidine-4-carboxamide and thionyl chloride is 1:15 moles, preferably 1:80 moles.

DETAILED DESCRIPTION OF THE INVENTION

The present invention provides an improved process for producing cyanopiperidine. The process of the present invention is advantageous over known processes because it involves a single step reaction, use of a single solvent and better yields and selectivity, by suppressing the formation of unwanted products.

As discussed above, the present invention provides a process for producing a cyanopiperidine, comprising treating a piperidine carboxamide with thionyl chloride. The piperidine carboxamide may be 2-, 3- or 4-piperidine carboxamide which produces 2-, 3- or 4-cyanopiperidine, respectively.

In a preferred embodiment, the piperidine-4-carboxamide used for the preparation of 4-cyanopiperidine is of high purity (M.p.–144-149° C.) and moisture contents of less than 0.2-2% preferably 0.2-1.0%.

In a preferred embodiment, the process of the present invention comprises treating piperidine-4-carboxamide with thionyl chloride in a ratio of 1:15 moles, preferably 1:80 moles, at a temperature of 10°-150° C., preferably 20°-100° C., for 4-6 hours, drying the resultant product and adding 46% caustic lye to adjust to pH 12-13, extracting the resultant alkaline mass with a suitable non-polar solvent at a temperature of 20°-25° C., separating the organic layer and distilling the concentrated mass through high vacuum, cooling the reaction mass to 30°-35° C., pouring into crushed ice and treating with excess of 46% caustic lye to adjust to a pH between 12 and 13. The alkaline reaction mass is extracted with suitable aromatic hydrocarbon solvents, like benzene, toluene and xylene etc. The organic layer is separated and concentrated to recover solvent. The concentrated mass thus obtained is distilled under vacuum to obtain pure 4-cyanopiperidine in 60-65% molar yield. Thus, the product is obtained in at least 60% molar yield. The purity of the cyanopiperidine is at least 98%.

The temperature range described above, i.e., 100-150° C., includes all specific values and subranges therebetween, such as 20°, 30°, 40°, 50°, 60°, 70°, 80°, 90°, 100° and 110° C. The molar ratio of the piperidine carboxamide and thionyl chloride may be between 1:4 to 1:80 moles, inclusive of all specific values and subranges therebetween, such as 1:5, 1:8, 1:10, 1:20, 1:25, 1:40, 1:50, 1:60 and 1:70.

EXAMPLES

The following examples are illustrative of the invention and should not be construed as limiting the scope of the invention in any manner. It is understood that the variation of the process described below are possible without departing from the scope and spirit of the invention.

Example 1

Thionyl chloride 232 gm (molar ratio thionyl chloride: piperidine-4-carboxamide is 2.53:1) is taken in a 500 ml four-necked reaction flask, fitted with glass agitator and a condenser. A vent is provided at the condenser top passing through a 10% diluted solution of caustic lye to neutralize the vent gases. Piperidine-4-carboxamide 100 gm is added lot wise with continuous stirring over a period of 30 minutes, temperature increased from 32° to 65° C. due to the exothermicity of the reaction. The reaction mixture is maintained at 65°-70° C. for 3-4 hours and a sample is drawn and analyzed, 4-cyanopiperidine 94.78% Area, Piperidine-4-carboxamide=Nil is obtained. The reaction mass is cooled to room temperature and poured over 400 gm crushed ice by maintaining the temperature at 0°-10° C. Then, 160 gm (46% solution) caustic lye is added to the above mass while maintaining the temperature between 15°-20° C. and the pH is adjusted between 12 and 13. The alkaline reaction mass is extracted with (400 ml×4) toluene. The organic layer is separated and the solvent is recovered by atmospheric distillation. The concentrated mass is distilled under high vacuum (4-6 mm Hg) to obtain 52.5 gm (molar yield=61%) 4-cyanopipeiridne with purity 99.75%.

Example 2

Thionyl chloride 70 gm (molar ratio, thionyl chloride: piperidine-4-carboxamide (1.50:1) is taken in a 250 ml 4-necked glass reactor fitted with an agitator and a condenser. A vent is provided at the condenser top passing through a 10% diluted solution of caustic lye to neutralize the vent gases. Piperidine-4-carboxamide 50 gm is added lot wise and the same procedure as in Example 1 is followed. 27 gm (molar yield 62.8%) 4-cyanopiperidine is obtained after final distillation with purity 99.0%.

Example 3

Thionyl chloride 465 gm (molar ratio, thionyl chloride: piperidine-4-carboxamide 10:1) is taken in a 500 ml, 4-necked glass reactor fitted with an agitator and a condenser. A vent is provided at the condenser top passing through a 10% diluted solution of caustic lye to neutralize the vent gases. Piperidine-4-carboxamide 48 gm is added lot-wise and after following the same procedure as in Example 1, 13.5 gm (molar yield 32.7%) of 4-cyanopiperidine is obtained with 98.75%

Certain modifications and improvements of the disclosed invention will occur to those skilled in the art without departing from the scope of invention, which is limited only by the appended claims.

This application is based on Indian patent application Serial No. 2035/DEL/2004, filed on Oct. 18, 2004, and incorporated herein by reference.

We claim:

1. A process for producing a cyanopiperidine, comprising:
   treating a piperidine carboxamide with thionyl chloride to produce a reaction mass, wherein the molar ratio of piperidine carboxamide to thionyl chloride is 1:15,
   neutralizing the reaction mass,
   extracting the neutralized reaction mass with an aromatic hydrocarbon solvent,
   distilling out the hydrocarbon solvent to produce a crude product, and
   distilling the crude product under vacuum to obtain the cyanopiperidine.

2. The process according to claim 1, wherein the aromatic hydrocarbon solvent is benzene, toluene or xylene.

3. The process according to claim 1, wherein the treatment of the piperidine carboxamide with the thionyl chloride takes place in a single step.

4. The process according to claim 1, wherein the treatment of the piperidine carboxamide with the thionyl chloride is conducted at a temperature of 10-150° C.

5. The process according to claim 1, wherein the treatment of the piperidine carboxamide with the thionyl chloride is conducted at a temperature of 20-100° C.

6. The process according to claim 1, wherein the cyanopiperidine is obtained in at least 60% molar yield.

7. The process according to claim 1, wherein the cyanopiperidine is 4-cyanopiperidine and the piperidine carboxamide is 4-piperidine carboxamide.

8. The process according to claim 1, wherein the cyanopiperidine is 3-cyanopiperidine and the piperidine carboxamide is 3-piperidine carboxamide.

9. The process according to claim 1, wherein the cyanopiperidine is 2-cyanopiperidine and the piperidine carboxamide is 2-piperidine carboxamide.

10. The process according to claim 1, wherein the cyanopiperidine has a purity of more than 98%.

* * * * *

UNITED STATES PATENT AND TRADEMARK OFFICE
CERTIFICATE OF CORRECTION

PATENT NO. : 7,348,435 B2
APPLICATION NO. : 11/195728
DATED : March 25, 2008
INVENTOR(S) : Vijay Kumar Kaushik et al.

It is certified that error appears in the above-identified patent and that said Letters Patent is hereby corrected as shown below:

In Column 2, Line 23:
"preferably 1:80 moles" should read --preferably 1:8 moles--;

Line 46:
"preferably 1:80" should read --preferably 1:8--;

Line 63:
"100-150°C" should read --10-150°C--;

Line 67:
"1:4 to 1:80 moles" should read --1:4 to 1:8 moles--.

In Column 3, Lines 2-3:
"1:5, 1:8, 1:10, 1:20, 1:25, 1:40, 1:50, 1:60 and 1:70" should read --1:5, 1:6 and 1:7--.

Signed and Sealed this

Ninth Day of December, 2008

JON W. DUDAS
*Director of the United States Patent and Trademark Office*